(12) United States Patent
Wilson et al.

(10) Patent No.: US 8,501,208 B2
(45) Date of Patent: Aug. 6, 2013

(54) MICROENCAPSULATED OILS FOR CONTROLLING PESTICIDE SPRAY DRIFT

(75) Inventors: Stephen L. Wilson, Zionsville, IN (US); Brandon M. Downer, Greenfield, IN (US); Kuide Qin, Westfield, IN (US); Lei Liu, Carmel, IN (US); Holger Tank, Zionsville, IN (US); Mei Li, Westfield, IN (US); David G. Ouse, Indianapolis, IN (US); Hong Zhang, Carmel, IN (US)

(73) Assignee: Dow AgroSciences LLC., Indianapolis, IN (US)

( * ) Notice: Subject to any disclaimer, the term of this patent is extended or adjusted under 35 U.S.C. 154(b) by 0 days.

(21) Appl. No.: 13/154,577

(22) Filed: Jun. 7, 2011

(65) Prior Publication Data

US 2011/0301033 A1  Dec. 8, 2011

Related U.S. Application Data

(60) Provisional application No. 61/352,505, filed on Jun. 8, 2010.

(51) Int. Cl.
  *A01N 25/34*  (2006.01)
  *A01N 57/18*  (2006.01)
  *A01N 43/68*  (2006.01)
  *A61K 9/48*  (2006.01)

(52) U.S. Cl.
  USPC ............ 424/408; 424/451; 504/203; 504/323

(58) Field of Classification Search
  None
  See application file for complete search history.

(56) References Cited

U.S. PATENT DOCUMENTS

| 4,999,048 | A | 3/1991 | Freepons |
| 6,214,771 | B1 | 4/2001 | Dexter |
| 6,797,673 | B1 | 9/2004 | Worthley et al. |
| 2006/0003897 | A1* | 1/2006 | Bell .............................. 504/364 |

FOREIGN PATENT DOCUMENTS

| WO | WO/02/068111 A1 | 9/2002 |
| WO | WO/2004/098767 A1 | 11/2004 |
| WO | WO2008/101818 A2 | 8/2008 |
| WO | WO 2010/026127 A1 | 3/2010 |
| WO | WO/2011/156320 | 12/2011 |

OTHER PUBLICATIONS

"Drift Control Adjuvants in Spray Applications: Performance and regulatory aspects." Proc. Third Latin American Symposium on Agricultural Adjuvans, Sao Paolo, Brazil.

"Chemistry and Technology of Agrochemical Formulations," P.J. Mulqueen; D.A. Knowles, editor, (Kluwer Academic Publishers, 1998. pp. 132-147.

Strainer, et al.: "Droplet Size Spectra and Drift Effect of Two Phenmedipham Formulations and Four Adjuvants Mixtures", Crop Protection, Elsevier Science, GB, vol. 25, No. 12, Dec. 1, 2006, pp. 1238-1243.

* cited by examiner

*Primary Examiner* — Alton Pryor
(74) *Attorney, Agent, or Firm* — Michael R. Asam

(57) ABSTRACT

Spray drift during the application of agricultural chemicals is reduced by incorporating microencapsulated oils into the aqueous solution or mixture to be sprayed.

5 Claims, No Drawings

MICROENCAPSULATED OILS FOR CONTROLLING PESTICIDE SPRAY DRIFT

CROSS REFERENCE TO RELATED APPLICATIONS

This application claims the benefit of U.S. Provisional Patent Application Ser. No. 61/352,505 filed Jun. 8, 2010.

FIELD OF THE INVENTION

The present invention concerns a novel method to reduce spray drift during the application of agricultural chemicals by incorporating microencapsulated oil compositions into the aqueous spray mixture.

BACKGROUND OF THE INVENTION

Agricultural spraying by economical and available technologies uses hydraulic spray nozzles that inherently produce a wide spectrum of spray droplet sizes. The potential for these spray droplets to drift from the initial, desired site of application is found to be a function of droplet size, with smaller droplets having a higher propensity for off-target movement. Significant research efforts, involving numerous field trials, wind tunnel tests and subsequent generation of predictive math models have led to a greatly enhanced understanding of the relationship between spray droplet size and potential for off-target drift. Although other factors such as meteorological conditions and spray boom height contribute to the potential for drift, spray droplet size distribution has been found to be a predominant factor. Teske et. al. (Teske M. E., Hewitt A. J., Valcore, D. L. 2004. *The Role of Small Droplets in Classifying Drop Size Distributions* ILASS Americas 17$^{th}$ Annual Conference: Arlington Va.) have reported a value of <156 microns ($\mu$) as the fraction of the spray droplet distribution that contributes to drift. Wolf (www.bae.ksu.edu/faculty/wolf/drift-.htm) cites a value of <200$\mu$ as the driftable fraction. A good estimation of droplet size likely to contribute to drift, therefore, is the fraction below about 150$\mu$.

The negative consequences of off-target movement can be quite pronounced. Some herbicides have demonstrated very sensitive phytotoxicity to particular plant species at extremely low parts per million (ppm) or even parts per billion (ppb) levels, resulting in restricted applications around sensitive crops, orchards and residential plantings. For example, the California Dept of Pesticide Regulation imposes buffers of ½-2 miles for propanil containing herbicides applied aerially in the San Joaquin valley.

High molecular weight, water-soluble polymers are sometimes added to spray compositions as a tank mix to increase droplet size and thereby reduce drift (see, for example, WO 2008/101818 A2 and U.S. Pat. No. 6,214,771 B1). However, high molecular weight, water-soluble polymers are not entirely satisfactory because they do not always work with many aerially applied herbicide tank mixtures, due to pump shear, wind shear and other performance issues, which are more pronounced in high speed aerial application conditions. See Hewitt, A. J. (2003) Drift Control Adjuvants in Spray Applications: Performance and Regulatory Aspects. *Proc. Third Latin American Symposium on Agricultural Adjuvants, Sao Paolo, Brazil.*

SUMMARY OF THE INVENTION

It has now been found that by incorporating microencapsulated oils into an aqueous agricultural spray mixture, spray drift during application can be reduced. The term "microencapsulated oil" refers herein to both the microcapsule and the oil contained within the microcapsule.

The present invention concerns a method to reduce spray drift during the application of an aqueous pesticidal spray mixture which comprises incorporating into the aqueous pesticidal spray mixture from about 0.01 to about 5 percent vol/vol of a microencapsulated oil. The reduction in spray drift may result from a variety of factors including a reduction in the production of fine spray droplets (<150$\mu$ in diameter) and an increase in the volume median diameter (VMD) of the spray droplets. For a given spray apparatus, application and conditions, and based on the microencapsulated oil used, the median diameter of the plurality of spray droplets is increased above that of an aqueous spray composition without said microencapsulated oil.

One embodiment of the invention is an aqueous in-can premix composition which comprises from about 5 to about 70 weight percent of at least one pesticide, and from about 0.05 to about 10 weight percent of the microencapsulated oil. The aqueous, in-can, premix composition is preferably a solution, emulsion or a suspension formulation or mixture thereof containing the microencapsulated oil suspended in the formulation.

A further embodiment of the invention is an aqueous in-can premix composition of improved physical stability which comprises from about 5 to about 70 weight percent of at least one pesticide and from about 0.05 to about 10 weight percent of the microencapsulated oil, wherein the preferred particle size of the microencapsulated oil is within the range of about 0.1 to about 1$\mu$, preferably from about 0.1 to about 0.5$\mu$. The aqueous in-can premix composition is preferably a solution, emulsion or a suspension formulation or mixture thereof containing the microencapsulated oil suspended in the formulation.

DETAILED DESCRIPTION OF THE INVENTION

The method to reduce spray drift by incorporating microencapsulated oils into an aqueous agricultural spray mixture applies to the application of any pesticide or crop protection agent including herbicides, fungicides and insecticides. Particularly preferred herbicides to which this method applies include cyhalofop-butyl, penoxsulam, flumetsulam, cloransulam-methyl, florasulam, pyroxsulam, diclosulam, fluoroxypyr, clopyralid, acetochlor, triclopyr, isoxaben, 2,4-D, MCPA, MCPB, dicamba, MSMA, oxyfluorfen, oryzalin, trifluralin, aminopyralid, atrazine, picloram, tebuthiuron, pendimethalin, propanil, glyphosate and glufosinate. Particularly preferred insecticides to which this method applies include organophosphates such as chlorpyrifos, MAC's such as halofenozide, methoxyfenozide and tebufenozide, pyrethroids such as gamma-cyhalothrin and deltamethrin, sulfoximines such as sulfoxaflor and biologically derived pesticides such as spinosad and spinetoram. Particularly preferred fungicides to which this method applies include mancozeb, myclobutanil, fenbuconazole, zoxamide, propiconazole, quinoxyfen and thifluzamide. The present invention is particularly useful for the application of herbicides, most particularly with herbicides that are subject to restricted applications around sensitive crops such as 2,4-D, dicamba, glyphosate and glufosinate.

Microencapsulated oils of the present invention are prepared by employing interfacial polycondensation encapsulation technology. Use of encapsulation technology in the formulation of agricultural active ingredients is well known to those skilled in the art. See, for example, P. J. Mulqueen in, "Chemistry and Technology of Agrochemical Formulations", D. A. Knowles, editor, (Kluwer Academic Publishers, 1998), pages 132-147, and references cited therein for a discussion of the use of microencapsulation in the formulation of pesticide active ingredients. In general, microcapsules can be prepared by an interfacial polycondensation between at least one oil soluble monomer selected, for example, from the group consisting of: diisocyanates, polyisocyanates, diacid chlorides, polyacid chlorides, sulfonyl chlorides, and chloroformates and at least one water soluble monomer selected, for example, from the group consisting of, diamines, polyamines, diols, and polyols. Typical microcapsule formulations may be derived, for example, from the interfacial polycondensation between isocyanates and either amines or alcohols to provide, respectively, polyurea or polyurethane microcapsule compositions.

Microencapsulated oils of the present invention may be prepared by first emulsifying an organic phase comprised of an oil and an oil soluble monomer in an aqueous phase comprised of suitable surfactants and water. The emulsion may be formed by homogenizing the oil-water mixture by the use of low or high pressure homogenization until the desired size of oil droplets suspended in the water is obtained. The water soluble monomer is then added to the mixture and reacts with the oil soluble monomer at the water-oil interface of the oil droplets to form the capsule wall enclosing the oil droplet. For example, by carefully adjusting the length of time that the mixture is homogenized and/or by adjusting the speed or pressure of the homogenizer, it is possible to produce microencapsulated oils of varying capsule sizes (diameter) and wall thicknesses. Similarly, the amount of monomer, cross-linking agents, emulsifying agents, buffer, and the like can be adjusted to create microencapsulated formulations having varying capsule sizes and wall thicknesses that can be readily prepared by one of normal skill in the art.

The microencapsulated oils of the present invention generally have capsules with average diameters that range from about 0.1 to about $20\mu$. The lower size limit of this range is based on the relative difficulty or impracticality of preparing very small capsules ($<0.1\mu$ average diameter) without the realization of any significant added performance benefits, whereas the upper size limit of this range is based on general knowledge in the art that suspensions of larger sized capsules ($>20\mu$ average diameter) can have physical stability issues as evidenced by their tendency to form creams.

The polymeric capsule wall of the microencapsulated oils of the present invention may comprise from about 0.5 to about 20 weight percent of the total weight of the microcapsule and its oil contents.

The oil used in the microencapsulated oils of the present invention is generally comprised of a water immiscible solvent, such as but not limited to, one or more of petroleum distillates such as aromatic hydrocarbons derived from benzene, such as toluene, xylenes, other alkylated benzenes and the like, and naphthalene derivatives; aliphatic hydrocarbons such as hexane, octane, cyclohexane, and the like; mineral oils from the aliphatic or isoparaffinic series, and mixtures of aromatic and aliphatic hydrocarbons; halogenated aromatic or aliphatic hydrocarbons; vegetable, seed or animal oils such as soybean oil, rape seed oil, olive oil, castor oil, sunflower seed oil, coconut oil, corn oil, cotton seed oil, linseed oil, palm oil, peanut oil, safflower oil, sesame oil, tung oil and the like, and $C_1$-$C_6$ mono-esters derived from vegetable, seed or animal oils; dialkyl amides of short and long chain, saturated and unsaturated carboxylic acids; $C_1$-$C_{12}$ esters of aromatic carboxylic acids and dicarboxylic acids, and $C_1$-$C_{12}$ esters of aliphatic and cyclo-aliphatic carboxylic acids.

The oil contained in the microcapsules of the present invention may optionally be used as a carrier for pesticides or other ingredients. These pesticides or other ingredients, may be dissolved or dispersed in the oil, and may be selected from acaricides, algicides, antifeedants, avicides, bactericides, bird repellents, chemosterilants, fungicides, herbicide safeners, herbicides, insect attractants, insect repellents, mammal repellents, mating disrupters, molluscicides, plant activators, plant growth regulators, rodenticides, synergists, defoliants, desiccants, disinfectants, semiochemicals, and virucides.

Oil soluble monomers used to prepare the microencapsulated oils of the present invention may include, but are not limited to, the groups consisting of diisocyanates, polyisocyanates, diacid chlorides, polyacid chlorides, sulfonyl chlorides, and chloroformates. Preferred oil soluble monomers are diisocyanates and polyisocyanates such as, for example, PAPI® 27 methylene diphenyl diisocyanate (registered trademark of the Dow Chemical Company), isophorone diisocyanate and hexamethylene diisocyanate.

Water soluble monomers of the present invention which may be used to react with the oil soluble monomers to form the capsule wall at the oil-water interface may include, but are not limited to, the groups consisting of diamines, polyamines, diols, and polyols.

Water soluble or dispersible surfactants used to prepare the microencapsulated oils of the present invention may include one or more surfactants. The surfactants can be anionic, cationic or nonionic in character and can be employed as emulsifying agents, wetting agents, dispersing agents, or for other purposes. It has also been shown that the choice of the surfactants used for the preparation of the capsules of the present invention is significant to their performance in reducing spray drift. Suitable surfactants include, but are not limited to, lignosulfonates such as, for example, Kraftsperse 25M, polymethyl methacrylate-polyethylene glycol graft copolymers such as, for example, Atlox 4913 and alcohol ethoxylates such as, for example, Tergitol 15-S-7.

The microencapsulated oils of the present invention can be incorporated into the aqueous pesticidal spray mixture by being tank-mixed directly with the diluted pesticidal formulation. The microencapsulated oil is incorporated into the aqueous spray mixture at a concentration from about 0.01 to about 5 volume percent of the final spray volume, preferably from about 0.05 to about 1.0 volume percent of the final spray volume, and most preferably from about 0.05 to about 0.2 volume percent of the final spray volume.

The present method reduces off-target movement of the pesticide spray in both aerial and ground applications.

The optimum spray droplet size depends on the application for which the composition is used. If droplets are too large, there will be less coverage by the spray; i.e, large droplets will land in certain areas while areas in between will receive little or no spray composition. The maximum acceptable droplet size may depend on the amount of composition being applied per unit area and the need for uniformity in spray coverage. Smaller droplets provide more even coverage, but are more prone to drift during spraying. If it is particularly windy during spraying, larger droplets may be preferred, whereas on a calmer day smaller droplets may be preferred.

The spray droplet size may also depend on the spray apparatus, e.g., nozzle size and configuration. In any event, for a given spray apparatus, application, and conditions, and based on the microencapsulated oil used, the median diameter of the plurality of spray droplets is increased above that of a spray composition without said microencapsulated oil.

In addition to the method set forth above, the present invention also embraces aqueous in-can premix compositions comprising from about 5 to about 70 weight percent, and preferably from about 20 to about 60 weight percent of at least one pesticide and from about 0.05 to about 10 weight percent of the microencapsulated oil. The aqueous in-can premix composition is preferably a solution, emulsion or a suspension formulation or mixture thereof containing the microencapsulated oil suspended in the formulation. Preferred pesticides that may be utilized in an aqueous in-can premix composition include the herbicides 2,4-D, aminopyralid, triclopyr, picloram, dicamba, glyphosate and glufosinate, and derivatives thereof.

A further embodiment of the invention is an aqueous in-can premix composition of improved physical stability which comprises from about 5 to about 70 weight percent, preferably from about 20 to about 60 weight percent of at least one pesticide and from about 0.05 to about 10 weight percent of the microencapsulated oil. The aqueous in-can premix composition is preferably a solution, emulsion or a suspension formulation or mixture thereof containing the microencapsulated oil suspended in the formulation. The aqueous in-can premix composition of improved stability is comprised of microcapsules with an average diameter from about 0.1 to about 1μ, preferably from about 0.1 to about 0.5μ. This composition shows improved physical stability compared to compositions containing microcapsules of oil with average diameters of greater than about 1μ or compositions that contain emulsified oils.

Optionally, the compositions of the present invention may contain a surfactant. The surfactants can be anionic, cationic or nonionic in character. Typical surfactants include salts of alkyl sulfates, such as diethanolammonium lauryl sulfate; alkylarylsulfonate salts, such as calcium dodecylbenzenesulfonate; alkyl and/or arylalkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; ethoxylated amines, such as tallowamine ethoxylated; betaine surfactants, such as cocoamidopropyl betaine; polyethylene glycol esters of fatty acids, such as polyethylene glycol stearate; block copolymers of ethylene oxide and propylene oxide; salts of mono and dialkyl phosphate esters; and mixtures thereof. The surfactant or mixture of surfactants is usually present at a concentration of from about 1 to about 20 weight percent of the formulation.

In addition to the compositions set forth above, the present invention also embraces compositions containing one or more additional compatible ingredients. These additional ingredients may include, for example, one or more pesticides or other ingredients, which may be dissolved or dispersed in the composition or may be dissolved or dispersed in the microencapsulated oil of the present invention, and may be selected from acaricides, algicides, antifeedants, avicides, bactericides, bird repellents, chemosterilants, fungicides, herbicide safeners, herbicides, insect attractants, insect repellents, mammal repellents, mating disrupters, molluscicides, plant activators, plant growth regulators, rodenticides, synergists, defoliants, desiccants, disinfectants, semiochemicals, and virucides. Also, any other additional ingredients providing functional utility such as, for example, dyes, stabilizers, fragrants, viscosity-lowering additives, and freeze-point depressants may be included in these compositions.

The following Examples illustrate the invention.

EXAMPLE 1

An organic phase comprised of 132.68 g of methyl soyate and 13.95 g of PAPI® 27 methylene diphenyl diisocyanate (registered trademark of the Dow Chemical Company) was emulsified into an aqueous phase comprised of 30.0 g of Atlox® 4913 polymeric surfactant (registered trademark of Croda Inc.), 7.50 g of Tergitol® 15-S-7 nonionic surfactant (registered trademark of the Dow Chemical Company), 0.39 g of Proxel® GXL preservative (registered trademark of Arch Chemicals Inc.) and 112.13 g of deionized water using a Silverson homogenizer. The resulting coarse emulsion was passed two times through a Niro high pressure homogenizer at 800-1200 bar (80,000-120,000 kPa). The polyurea capsule wall was then formed by adding 3.33 g of a 10% aqueous ethylenediamine solution with moderate stirring. The resulting volume median particle size of the capsule suspension was 0.34μ as measured using a Malvern Mastersizer 2000 laser diffraction particle analyzer.

To 3.68 g of the above methyl soyate capsule suspension was added in order: 0.85 g of deionized water, 10.66 g of 2,4-D dimethyethanolammonium (DMEA) salt solution (53.6% a.e.), and 14.27 g of glyphosate dimethylammonium (DMA) salt solution (42.2% a.e.) to yield, after thorough mixing, a creamy off-white emulsion which did not phase separate after extended storage (30 days) on the laboratory bench.

A 2 wt % solution of the methyl soyate/2,4-D DMEA/glyphosate DMA concentrate in water was prepared for testing its spray performance. The solution was sprayed using a Teejet 8002 flat fan nozzle at 40 psi and the spray droplet size distribution measurement performed with a Sympatec laser diffraction particle analyzer. The tip of the nozzle was situated 12 inches above the path of the laser beam of the Sympatec. The percentage of driftable fines was expressed as the volume percentage of spray droplets below 150μ. The results, along with that for a deionized water control, are shown in Table 1.

TABLE 1

| Spray Sample | Spray Droplets VMD, μ | Volume Percent Driftable Fines <150μ |
|---|---|---|
| deionized water | 161 | 45.6% |
| 2 wt % solution of 2,4-D DMEA + glyphosate DMA + methyl soyate capsules | 268 | 16.6% |

EXAMPLE 2

An organic phase comprised of 340.53 g of methyl soyate and 9.05 g of PAPI® 27 (registered trademark of the Dow Chemical Company) was emulsified into an aqueous phase comprised of 96.0 g of Atlox® 4913 (registered trademark of Croda Inc.), 24.0 g of Tergitol® 15-S-7 (registered trademark of the Dow Chemical Company), 1.20 g of Proxel® GXL (registered trademark of Arch Chemicals Inc.) and 358.8 g of deionized water using a Silverson homogenizer. The speed on the homogenizer was increased until the volume median droplet size was ca. 0.8μ. The polyurea capsule wall was then formed by adding 21.73 g of a 10% aqueous ethylenediamine solution with moderate stirring. The resulting volume median particle size of the capsule suspension was 0.72μ.

A herbicide concentrate comprised of 456 g ae/L 2,4-D choline salt and 10 wt % of the above methyl soyate microcapsule suspension was prepared as follows: a sample jar was charged with 39.91 g of a 45.7% ae 2,4-D choline solution (prepared by mixing equimolar amounts of 2,4-D and choline hydroxide in water). To this sample jar, 4.74 g of the above methyl soyate capsule suspension (40% w/w oil) was added. The sample was then stirred for approximately 1 minute under moderate mixing. Lastly, 2.74 g of deionized water was added and the sample was stirred for approximately 2 minutes under moderate mixing until homogenous to yield a creamy off-white emulsion which did not phase separate after extended storage (30 days) on the laboratory bench.

A 1.25% v/v spray solution dilution of the above herbicide concentrate was then prepared. A sample jar was first charged with 296.25 mL of deionized water. Then, 3.75 mL of the herbicide concentrate was added. The sample jar was lightly shaken by hand until the mixture was homogenous. The diluted spray solution was then sprayed following the same procedure and settings as described in Example 1. The results are shown in Table 2, and are compared to a 1.25% spray solution of 2,4-D choline without the methyl soyate capsule suspension.

TABLE 2

| Spray Sample | Spray Droplets VMD, μ | Volume Percent Driftable Fines <150μ |
|---|---|---|
| 1.25% spray solution of 2,4-D choline | 152 | 49.0% |
| 1.25% spray solution of 2,4-D choline + methyl soyate capsules | 274 | 16.5% |

EXAMPLE 3

The spray performance of Ignite® 280 SL herbicide (registered trademark of Bayer CropScience; 2.34 lb ae/gal glufosinate-ammonium) with ammonium sulfate (AMS) was compared with and without the addition of the methyl soyate capsule suspension prepared in Example 2. A sample jar was charged with 284.33 g of deionized water, 15.03 g of a 40% w/w aqueous ammonium sulfate and, lastly, 3.97 g of Ignite® 280 SL. The sample jar was shaken by hand until homogenous. To make the capsule-containing spray solution, a second sample jar was charged with 283.57 g of deionized water, 15.03 g of a 40% w/w aqueous ammonium sulfate solution, 3.97 g of Ignite® 280 SL, and, lastly, 0.76 g of the methyl soyate capsule suspension prepared in Example 2. The second sample jar was shaken by hand until homogenous. The solutions were then sprayed following the same procedure and settings as described in Example 1. The results are shown in Table 3.

TABLE 3

| Spray Sample | Spray Droplets VMD, μ | Volume Percent Driftable Fines <150μ |
|---|---|---|
| spray solution of Ignite® + AMS | 140 | 54.3% |
| spray solution of Ignite® + AMS + methyl soyate capsules | 257 | 19.2% |

EXAMPLE 4

The spray performance of Clarity® herbicide (registered trademark of BASF Corporation; 4 lb ae/gal dicamba diglycolamine) was compared with and without addition of the methyl soyate capsule suspension prepared in Example 2. A sample jar was charged with 298.14 mL of deionized water and 1.86 mL of Clarity® herbicide. The sample was shaken by hand until homogenous. To make the capsule-containing spray solution, a second sample jar was charged with 297.38 g of deionized water, 2.29 g (1.86 mL) of Clarity® herbicide, and 0.76 g of the methyl soyate microcapsule suspension prepared in Example 2. The sample was then shaken by hand until homogenous. The solutions were then sprayed following the procedure and settings as described in Example 1. The results are shown in Table 4.

TABLE 4

| Spray Sample | Spray Droplets VMD, μ | Volume Percent Driftable Fines <150μ |
|---|---|---|
| spray solution of Clarity® | 163 | 45.1% |
| spray solution of Clarity® + methyl soyate capsules | 284 | 15.7% |

We claim:

1. A method to reduce spray drift during the application of an aqueous pesticidal spray mixture which comprises incorporating into the aqueous herbicide spray mixture from about 0.01 to about 5 percent vol/vol of a microencapsulated oil, wherein the polymeric capsule wall of the microencapsulated oil comprises from about 0.5 to about 20 weight percent of the total weight of the microcapsule and its oil contents and the production of fine spray droplets smaller than 150μ in diameter is reduced and the volume mean diameter (VMD) of the spray droplets in increased compared to when the microencapsulated oil is not present.

2. The method of claim 1 in which the herbicide is at least one of a salt of 2,4-D, dicamba, glyphosate or glufosinate.

3. The method of claim 1 in which the capsules of the microencapsulated oil have an average diameter range from about 0.1 to about 20μ.

4. An in-can premix aqueous composition which comprises from about 5 to about 70 weight percent of at least one herbicide and from about 0.05 to about 10 weight percent of a microencapsulated oil suspended in the composition, wherein the capsule size of the microencapsulated oil is from about 0.1 to about 1μ and, when the in-can premix aqueous composition is sprayed, the production of fine spray droplets smaller than 150μ in diameter is reduced and the volume mean diameter (VMD) of the spray droplets in increased compared to when the microencapsulated oil is not present.

5. The composition of claim 4 in which the herbicide is at least one of a salt of 2,4-D, dicamba, glyphosate or glufosinate.

* * * * *